United States Patent
Xu et al.

(10) Patent No.: US 12,374,161 B2
(45) Date of Patent: Jul. 29, 2025

(54) ACTION RECOGNITION METHOD AND APPARATUS, TERMINAL DEVICE, AND MOTION MONITORING SYSTEM

(71) Applicant: HONOR DEVICE CO., LTD., Shenzhen (CN)

(72) Inventors: Teng Xu, Shenzhen (CN); Xiaohan Chen, Shenzhen (CN)

(73) Assignee: Honor Device Co., Ltd., Shenzhen (CN)

( * ) Notice: Subject to any disclaimer, the term of this patent is extended or adjusted under 35 U.S.C. 154(b) by 197 days.

(21) Appl. No.: 17/921,194

(22) PCT Filed: Sep. 14, 2021

(86) PCT No.: PCT/CN2021/118320
§ 371 (c)(1),
(2) Date: Oct. 25, 2022

(87) PCT Pub. No.: WO2022/057795
PCT Pub. Date: Mar. 24, 2022

(65) Prior Publication Data
US 2023/0206697 A1    Jun. 29, 2023

(30) Foreign Application Priority Data

Sep. 15, 2020 (CN) .......................... 202010970737.1

(51) Int. Cl.
*G06V 40/20* (2022.01)
*G06F 3/01* (2006.01)
(Continued)

(52) U.S. Cl.
CPC .............. *G06V 40/28* (2022.01); *G06F 3/017* (2013.01); *G06T 7/20* (2013.01); *G06V 10/25* (2022.01);
(Continued)

(58) Field of Classification Search
CPC ........ G06V 40/28; G06V 10/25; G06V 20/42; G06V 40/25; G06V 40/23; G06F 3/017;
(Continued)

(56) References Cited

U.S. PATENT DOCUMENTS 9,403,057 B2    8/2016  Shibuya
9,710,612 B2    7/2017  Sampathkumaran
(Continued)

FOREIGN PATENT DOCUMENTS

CN    101158883 A    4/2008
CN    102799263 A    11/2012
(Continued)

*Primary Examiner* — Tahmina N Ansari
(74) *Attorney, Agent, or Firm* — Fish & Richardson P.C.

(57) ABSTRACT

This application relates to the field of electronic technologies, and provides an action recognition method and apparatus, a terminal device, and a motion monitoring system. Characteristic extraction and action recognition are performed based on motion data collected by data collection apparatuses; a gait characteristic, a swing gesture characteristic, and an image action characteristic of a user are recognized by using a plurality of pieces of motion data; and a type of a hitting action of a player is determined based on the gait characteristic, the swing gesture characteristic, and the image action characteristic. In this way, the hitting action of the player in a motion process can be accurately recognized. This is conducive to performing comprehensive analysis on a comprehensive sports capability of the player, and is more helpful to formulating a personalized training plan for the player.

12 Claims, 9 Drawing Sheets

(51) Int. Cl.
- *G06T 7/20* (2017.01)
- *G06V 10/25* (2022.01)
- *G06V 20/40* (2022.01)

(52) U.S. Cl.
CPC .............. *G06V 20/42* (2022.01); *G06V 40/25* (2022.01); *G06T 2207/20084* (2013.01); *G06T 2207/30196* (2013.01); *G06T 2207/30221* (2013.01)

(58) Field of Classification Search
CPC ............. G06F 2218/12; G06T 7/20; G06T 2207/20084; G06T 2207/30196; G06T 2207/30221; A61B 5/02416; A61B 5/1122; A61B 5/6802; A61B 5/681; A61B 5/6829; A61B 2505/09; A61B 2562/0204; A61B 2562/0219; A61B 5/0077; A61B 5/112; A61B 5/1123; A61B 5/1124; A61B 5/6895; G09B 19/0038
See application file for complete search history.

(56) References Cited

U.S. PATENT DOCUMENTS

| | | | |
|---|---|---|---|
| 9,999,823 | B2 | 6/2018 | Chen et al. |
| 10,188,324 | B2 | 1/2019 | Matsunaga et al. |
| 10,248,985 | B2 | 4/2019 | Rohr et al. |
| 10,668,353 | B2 | 6/2020 | Mettler May |
| 10,737,158 | B2 | 8/2020 | Song et al. |
| 10,931,880 | B2 | 2/2021 | Byeon et al. |
| 11,263,919 | B2 | 3/2022 | Malhotra |
| 12,214,270 | B2 * | 2/2025 | Xu ........................ G01P 13/00 |
| 12,233,313 | B2 * | 2/2025 | Chen .................. A63B 71/0622 |
| 2015/0016685 | A1 * | 1/2015 | Matsunaga ............. G06F 18/21 382/103 |
| 2015/0029341 | A1 | 1/2015 | Sinha |
| 2015/0314164 | A1 | 11/2015 | Sampathkumaran |
| 2015/0352404 | A1 * | 12/2015 | Schwenger ........ A63B 69/0002 700/91 |
| 2016/0158598 | A1 | 6/2016 | Dolezel et al. |
| 2017/0182360 | A1 | 6/2017 | Chang et al. |
| 2019/0009133 | A1 | 1/2019 | Mettler May |
| 2019/0054347 | A1 | 2/2019 | Saigh et al. |
| 2019/0388728 | A1 | 12/2019 | Wang et al. |
| 2020/0005150 | A1 * | 1/2020 | Baughman ............. G06V 20/42 |
| 2021/0228959 | A1 | 7/2021 | Yan et al. |
| 2022/0362654 | A1 * | 11/2022 | Xu ...................... A63B 71/0619 |
| 2023/0206697 | A1 * | 6/2023 | Xu ........................ A61B 5/1123 |
| 2023/0271059 | A1 * | 8/2023 | Chen .................. A63B 24/0062 482/8 |

FOREIGN PATENT DOCUMENTS

| | | |
|---|---|---|
| CN | 102814033 A | 12/2012 |
| CN | 203017737 U | 6/2013 |
| CN | 104056441 A | 9/2014 |
| CN | 105210084 A | 12/2015 |
| CN | 105898241 A | 8/2016 |
| CN | 105912142 A | 8/2016 |
| CN | 106310609 A | 1/2017 |
| CN | 106581974 A | 4/2017 |
| CN | 106730771 A | 5/2017 |
| CN | 106778477 A | 5/2017 |
| CN | 107273857 A | 10/2017 |
| CN | 107281709 A | 10/2017 |
| CN | 107281717 A | 10/2017 |
| CN | 107982899 A | 5/2018 |
| CN | 108369646 A | 8/2018 |
| CN | 207898912 U | 9/2018 |
| CN | 108671505 A | 10/2018 |
| CN | 109260647 A | 1/2019 |
| CN | 109453501 A | 3/2019 |
| CN | 208927548 U | 6/2019 |
| CN | 110327595 A | 10/2019 |
| CN | 110558991 A | 12/2019 |
| CN | 111318009 A | 6/2020 |
| CN | 111369629 A | 7/2020 |
| CN | 111437583 A | 7/2020 |
| CN | 111514561 A | 8/2020 |
| DE | 10124242 A1 | 11/2002 |
| EP | 2953115 A1 | 12/2015 |
| KR | 20200077775 A | 7/2020 |
| WO | 2016025460 A1 | 2/2016 |

* cited by examiner

ACTION RECOGNITION METHOD AND APPARATUS, TERMINAL DEVICE, AND MOTION MONITORING SYSTEM

CROSS-REFERENCE TO RELATED APPLICATIONS

This application is a National Stage of International Application No. PCT/CN2021/118320, filed on Sep. 14, 2021, which claims priority to Chinese Patent Application No. 202010970737.1, filed on Sep. 15, 2020, both of which are hereby incorporated by reference in their entireties.

TECHNICAL FIELD

This application relates to the field of electronic technologies, and in particular, to an action recognition method and apparatus, a terminal device, and a motion monitoring system.

BACKGROUND

In a training process of a ball sport, for example, badminton, table tennis, or tennis, motion parameters of a player during hitting, such as a hitting type, hitting power, a hitting speed, and a quantity of hitting times, are measured, so that comprehensive physical quality of the player can be reflected. A comprehensive sports capability of the player can be evaluated based on these motion parameters, so that a personalized training plan can be formulated. Therefore, a type of a hitting action of the player during hitting needs to be accurately determined.

Currently, a plurality of wearable smart devices such as a power balance bracelet and step counting shoes appear in the market. However, currently, a wearable smart device in the market can obtain only basic parameters of a player in a process of a ball sport, such as a heart rate, a quantity of moved steps, and a moved distance, and cannot effectively recognize a hitting action of the player during hitting. Consequently, motion parameters of the player during hitting cannot be accurately measured. Therefore, an existing action recognition method cannot meet a requirement of performing comprehensive analysis on a comprehensive sports capability of the player in the ball sport.

SUMMARY

In view of this, this application provides an action recognition method, a terminal device, and a storage medium, so as to effectively recognize a hitting action of a player in a ball sport, and facilitate comprehensive analysis of a comprehensive sports capability of the player.

To achieve the foregoing objective, according to a first aspect, an embodiment of this application provides an action recognition method. The method may include: obtaining motion data, where the motion data includes first motion data, second motion data, and third motion data; obtaining a gait characteristic of a player in a motion process based on the first motion data; obtaining a swing gesture characteristic of the player in the motion process based on the second motion data; obtaining an image action characteristic of the player in the motion process based on the third motion data; and recognizing a hitting action of the player in the motion process based on the gait characteristic, the swing gesture characteristic, and the image action characteristic.

The first motion data is collected by a first data collection apparatus located at a first preset part of the player; the second motion data is collected by a second data collection apparatus disposed at a preset location of a racket; and the third motion data is collected by a third data collection apparatus disposed at a preset shooting location.

The first motion data is motion data that can reflect a lower limb action of the player. The first preset part of the player may be a lower leg or thigh location of the player, may be an ankle of the player, or may be another preset part in which the motion data of the lower limb action of the player can be collected.

The second motion data is motion data that can reflect an upper limb hitting action of the player. The preset location of the racket may be a racket handle, may be a racket shaft, or may be a racket head. This is not limited herein.

The third motion data is motion data that can reflect the image action characteristic of the player. For example, the third motion data may be a motion image of the player. The preset shooting location refers to a location in which the motion image of the player can be shot. The preset shooting location can be determined based on an actual requirement. Details are not described herein.

The gait characteristic of the player in the motion process includes, but is not limited to, a classification of the lower limb action and action parameters of the lower limb action. The swing gesture characteristic of the player in the motion process includes, but is not limited to, a type of a hand action, action parameters of the hand action, and whether hitting is effective. The image action characteristic includes, but is not limited to, a leg curl characteristic (there is leg curl and there is no leg curl) of the player in an image.

According to the action recognition method provided in this embodiment of this application, characteristic extraction and action recognition can be performed based on the motion data collected by the data collection apparatuses; a gait characteristic, a swing gesture characteristic, and an image action characteristic of a user are recognized by using a plurality of pieces of motion data; and a type of the hitting action of the player is determined based on the gait characteristic, the swing gesture characteristic, and the image action characteristic. In this way, the hitting action of the player in the motion process can be accurately recognized. This is conducive to performing comprehensive analysis on a comprehensive sports capability of the player, and is more helpful to formulating a personalized training plan for the player.

In a possible implementation of the first aspect, the first motion data includes foot acceleration data and foot angular velocity data, and the obtaining a gait characteristic of a player in a motion process based on the first motion data includes: drawing a foot acceleration waveform and a foot angular velocity waveform based on the foot acceleration data and the foot angular velocity data, and extracting a foot acceleration waveform characteristic, for example, a peak value, a trough value, a peak value location, or a trough value location; determining a departure location and a touchdown location of each step based on the foot acceleration waveform characteristic; performing single-step segmentation on the foot acceleration waveform and the foot angular velocity waveform based on the departure location and the touchdown location of each step; and determining, based on a segmented foot acceleration waveform and a segmented foot angular velocity waveform, a classification of a lower limb action corresponding to each step of the player and action parameters of the lower limb action.

The determining, based on a segmented foot acceleration waveform characteristic and a segmented foot angular velocity waveform characteristic, parameters of a lower limb action of the player may specifically include: calculating a hang duration of the player based on a departure moment and a touchdown moment, and calculating a moved distance, a moving speed, a vertical jump height, and the like of the player based on an integral value of a change of acceleration within an interval time between the departure moment and the touchdown moment.

In the foregoing implementation, the classification of the lower limb action corresponding to each step and the action parameters of the lower limb action are determined based on the foot acceleration data and the foot angular velocity data, so that an activity of a lower limb of the player in the motion process can be provided for analyzing the comprehensive sports capability of the player. This helps perform more comprehensive analysis on the comprehensive sports capability of the player.

In a possible implementation of the first aspect, the second motion data includes hand acceleration data, hand angular velocity data, and acoustic wave data, and the obtaining a swing gesture characteristic of the player in the motion process based on the second motion data includes: determining a classification of a hand action of the player in the motion process and action parameters of the hand action based on the hand acceleration data and the hand angular velocity data; performing effective hitting and missing recognition on each hand action of the player in the motion process based on the acoustic wave data; and determining the swing gesture characteristic of the player in the motion process based on the classification of the hand action of the player in the motion process and the action parameters of the hand action and based on the effective hitting and missing recognition performed on each hand action.

In the foregoing implementation, whether hitting is effective is determined based on an acoustic wave, and the classification of the hand action is determined based on the hand acceleration data and the hand angular velocity data, so that a quantity of effective hitting times of the player can be more accurately measured. This helps formulate a corresponding training plan for the player.

In a possible implementation of the first aspect, the third motion data includes a motion image of the player, and the obtaining an image action characteristic of the player in the motion process based on the third motion data includes: inputting the motion image of the player into a trained convolutional neural network model for processing, so as to obtain the image action characteristic corresponding to the motion image of the player.

In the foregoing implementation, the image action characteristic of the player is determined by using the convolutional neural network model. This can effectively improve efficiency of action classification.

In a possible implementation of the first aspect, the action recognition method further includes: when it is recognized that the hitting action is effective smash with leg curl, obtaining a leg curl angle, a hang duration, and a to-be-corrected jump height; and correcting the to-be-corrected jump height based on the hang duration and the leg curl angle. A jump height of the player is corrected, so that motion parameters of the player can be more accurately measured.

In a possible implementation of the first aspect, the motion data further includes fourth motion data, and correspondingly, the action recognition method further includes: determining physiological parameters of the player in the motion process based on the fourth motion data.

In the foregoing implementation, after the hitting action of the player in the motion process and action parameters corresponding to each hitting action are determined based on the first motion data, the second motion data, and the third motion data, motion intensity and a physical capability of the player can be further analyzed based on a heart rate determined based on the fourth motion data. This can implement more comprehensive evaluation on the comprehensive sports capability of the player.

According to a second aspect, an embodiment of this application provides an action recognition apparatus, including:

a first obtaining unit, configured to obtain motion data, where the motion data includes first motion data, second motion data, and third motion data; the first motion data is collected by a first data collection apparatus located at a first preset part of a player; the second motion data is collected by a second data collection apparatus disposed at a preset location of a racket; and the third motion data is collected by a third data collection apparatus disposed at a preset shooting location;

a second obtaining unit, configured to: obtain a gait characteristic of the player in a motion process based on the first motion data, obtain a swing gesture characteristic of the player in the motion process based on the second motion data, and obtain an image action characteristic of the player in the motion process based on the third motion data; and a recognition unit, configured to recognize a hitting action of the player in the motion process based on the gait characteristic, the swing gesture characteristic, and the image action characteristic.

In a possible implementation of the second aspect, the action recognition apparatus further includes a third obtaining unit, where the third obtaining unit is configured to obtain action parameters of the hitting action based on the motion data.

In a possible implementation of the second aspect, the first obtaining unit is further configured to obtain fourth motion data. Correspondingly, the action recognition apparatus further includes a physiological parameter determining unit, where the physiological parameter determining unit is configured to determine physiological parameters of the player in the motion process based on the fourth motion data.

In a possible implementation of the second aspect, the action recognition apparatus further includes a correction unit, where the correction unit is configured to: when the hitting action is effective smash with leg curl, correct a jump height of the player based on a hang duration and a leg curl angle.

According to a third aspect, an embodiment of this application provides a motion monitoring system. The motion monitoring system includes a first data collection apparatus, a second data collection apparatus, a third collection apparatus, and the action recognition apparatus according to the second aspect.

The first data collection apparatus, the second data collection apparatus, and the third data collection apparatus are separately communicatively connected to the action recognition apparatus.

The first data collection apparatus is configured to collect first motion data.

The second data collection apparatus is configured to collect second motion data.

The third data collection apparatus is configured to collect third motion data.

The action recognition apparatus is configured to recognize a hitting action of a player in a motion process based on the first motion data, the second motion data, and the third motion data.

In a possible implementation of the third aspect, the motion monitoring system further includes a fourth data collection apparatus, where the fourth data collection apparatus is communicatively connected to the action recognition apparatus.

The fourth data collection apparatus is configured to collect fourth motion data.

The action recognition apparatus is further configured to determine physiological parameters of the player in the motion process based on the fourth motion data.

According to a fourth aspect, an embodiment of this application provides a terminal device, including a memory, a processor, and a computer program that is stored in the memory and can run on the processor, where when the processor executes the computer program, the action recognition method according to the first aspect is implemented.

According to a fifth aspect, an embodiment of this application provides a computer-readable storage medium, where when the computer program is executed by a processor, the computer-readable storage medium stores a computer program, and the action recognition method according to the first aspect is implemented.

According to a sixth aspect, an embodiment of this application provides a computer program product, where when the computer program product runs on a terminal device, the terminal device is enabled to perform the action recognition method according to any one of the first aspect.

According to a seventh aspect, a chip is provided. The chip includes a processor, where when the processor executes instructions, the processor is configured to perform the action recognition method related to any design of the second aspect. The instructions may be from a memory inside the chip, or may be from a memory outside the chip. Optionally, the chip further includes an input/output circuit.

It may be understood that for beneficial effects of the second aspect to the seventh aspect, reference may be made to related descriptions in the first aspect. Details are not described herein again.

DESCRIPTION OF EMBODIMENTS

Figure 1:
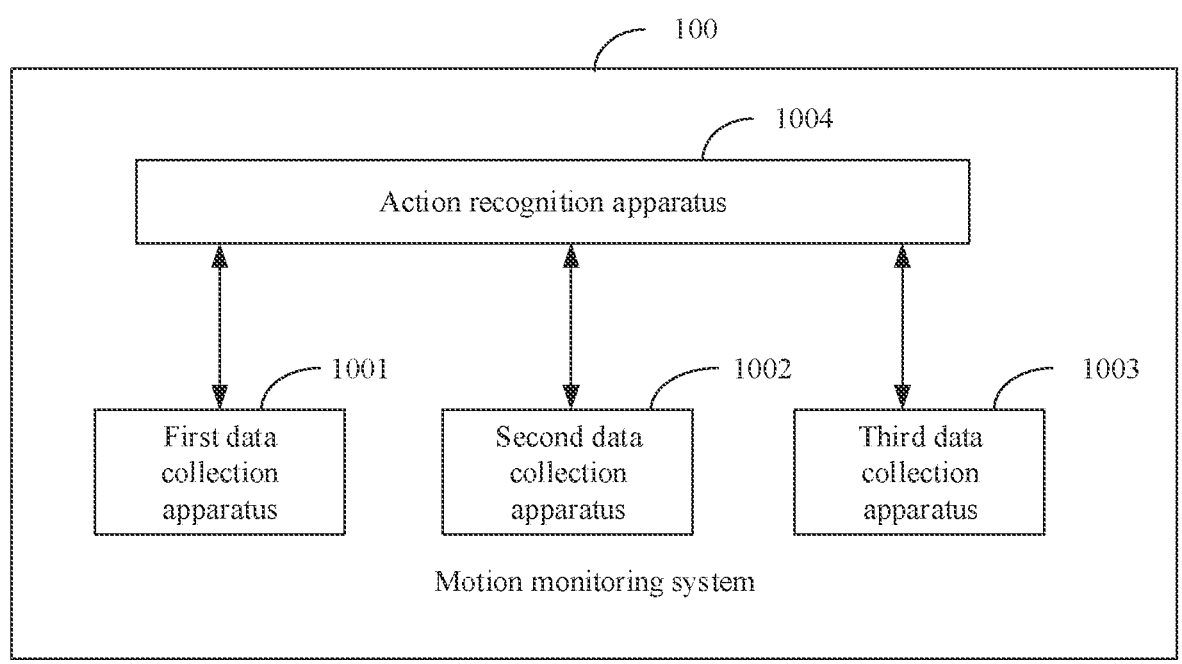
FIG. 1 is a schematic diagram of an architecture of a motion monitoring system applicable to an action recognition method according to an embodiment of this application.

In the following descriptions, specific details such as a specific system structure and a technology are proposed for description rather than limitation, to thoroughly understand embodiments of this application. However, a person skilled in the art should understand that this application may also be implemented in another embodiment without these specific details. In another case, detailed descriptions of a well-known system, apparatus, circuit, and method are omitted, to prevent needless details from impeding description of this application.

It should be understood that when being used in this specification and the appended claims of this application, the term "include" indicates presence of a described characteristic, entirety, step, operation, element and/or component, but does not rule out presence or addition of one or more other characteristics, entireties, steps, operations, elements, components and/or sets thereof.

It should also be understood that the term "and/or" used in this specification and the appended claims of this application means any combination and all possible combinations of one or more of listed associated items, and these combinations are included.

As used in this specification and the appended claims of this application, the term "if" may be interpreted according to the context as "when . . . ", "once", "determining in response to", or "detecting in response to". Similarly, the phrase "if it is determined that" or "if [a described condition or event] is detected" may be interpreted according to the context as "once it is determined that", "it is determined that in response to", "once [a described condition or event] is detected", or "[a described condition or event] is detected in response to".

In addition, in the descriptions of this specification and the appended claims of this application, the terms "first", "second", "third", and the like are merely used to distinguish between the descriptions, and cannot be understood as indicating or implying relative importance.

Referring to "one embodiment", "some embodiments", or the like that is described in this specification of this application means that specific characteristics, structures, or features described with reference to one or more embodiments are included in the one or more embodiments of this application. Therefore, the statements "in one embodiment", "in some embodiments", "in some other embodiments", "in some further embodiments", and the like that appear in different parts of this specification are not necessarily referred to a same embodiment, but mean "one or more but not all embodiments", unless otherwise specifically emphasized. The terms "include", "comprise", "have", and variations thereof all mean "include but be not limited to" unless otherwise specified in another manner.

Ball sports such as badminton, table tennis, and tennis are popular sports. An action recognition method and a motion monitoring system provided in the embodiments of this application are mainly used to recognize a hitting action in a ball sport, for example, badminton, table tennis, or tennis. The following uses badminton as an example to describe in detail the action recognition method and the motion monitoring system provided in the embodiments of this application.

Badminton is a competitive sport with diversified actions, and the actions are mainly completed by performing hand actions such as high clear, smash, lob, and chop. To evaluate a comprehensive sports capability of a badminton player and formulate a personalized training plan, motion parameters of the badminton player in a badminton motion process, such as a hitting type, hitting power, a hitting speed, and a quantity of hitting times, need to be measured. However, currently, a wearable smart device can obtain only basic parameters of a player in a process of a ball sport, such as a heart rate, a quantity of moved steps, and a moved distance. Consequently, a comprehensive sports capability of the player in a motion process cannot be analyzed based on these basic parameters.

Currently, some badminton action detection apparatuses appear in the market, such as a badminton action detection accessory disposed at a bottom of a badminton racket, where the badminton action detection accessory can recognize a badminton hitting action, and the like. However, because the badminton action detection accessory is disposed on the racket, only an upper limb hitting action can be detected, a lower limb action of a user cannot be detected, and vital sign parameters of the user cannot be detected. Therefore, in a current badminton hitting action recognition method, there is a problem that comprehensive scientific analysis and guide cannot be performed on a comprehensive sports capability of a player with reference to a lower limb action and vital sign parameters of a user.

To resolve the problem, in the current badminton hitting action recognition method, that comprehensive scientific analysis and guide cannot be performed on a comprehensive sports capability of a player with reference to a lower limb action and vital sign parameters of a user, embodiments of this application provide an action recognition method and a motion monitoring system.

FIG. 1 is a schematic diagram of an architecture of a motion monitoring system applicable to an action recognition method according to an embodiment of this application. As shown in FIG. 1, the motion monitoring system 100 may include a first data collection apparatus 1001, a second data collection apparatus 1002, a third data collection apparatus 1003, and an action recognition apparatus 1004. The first data collection apparatus 1001, the second data collection apparatus 1002, and the third data collection apparatus 1003 are separately communicatively connected to the action recognition apparatus 1004. The action recognition apparatus 1004 can perform characteristic extraction and action recognition based on motion data collected by the data collection apparatuses, recognize a gait characteristic, a swing gesture characteristic, and an image action characteristic of a user by using a plurality of pieces of motion data, and determine a type of a hitting action of a player based on the gait characteristic, the swing gesture characteristic, and the image action characteristic. In this way, the hitting action of the player in a motion process can be accurately recognized. This is conducive to performing comprehensive analysis on a comprehensive sports capability of the player, and is more helpful to formulating a personalized training plan for the player.

The action recognition apparatus 1004 can separately establish a wireless communication connection to the first data collection apparatus 1001, the second data collection apparatus 1002, and the third data collection apparatus 1003 in a short-range communication connection manner; or the action recognition apparatus 1004 can separately establish a wired communication connection to the first data collection apparatus 1001, the second data collection apparatus 1002, and the third data collection apparatus 1003 in a wired communication manner. A specific communication manner between the action recognition apparatus 1004 and the first data collection apparatus 1001, between the action recognition apparatus 1004 and the second data collection apparatus 1002, or between the action recognition apparatus 1004 and the third data collection apparatus 1003 is not limited in this embodiment of this application.

The short-range communication connection manner may be a Bluetooth connection, a near field communication (Near Field Communication. NFC) connection, a wireless-fidelity (Wireless-Fidelity, Wi-Fi) connection, a ZigBee (ZigBee) connection, or the like. To improve convenience of use of the player, a Bluetooth connection may be preferably used in this embodiment. A short-range communication identifier is a unique identifier related to a short-range communication connection of a terminal device. If the Bluetooth connection is used, the short-range communication identifier may be correspondingly a Bluetooth media access control (Media Access Control, MAC) address or another unique identifier of a Bluetooth device.

In this embodiment of this application, the first data collection apparatus 1001 is configured to collect first motion data. Specifically, the first data collection apparatus 1001 may be disposed at a first preset part of the player. The first motion data is motion data that can reflect a lower limb action of the player. The first data collection apparatus 1001 is further configured to send the first motion data collected in real time to the action recognition apparatus 1004 that is communicatively connected to the first data collection apparatus 1001.

In this embodiment of this application, the first preset part of the player may be a lower leg or thigh location of the player, may be an ankle of the player, or may be another preset part in which the motion data of the lower limb action of the player can be collected. For ease of understanding, the following uses an example in which the first preset part is the ankle of the player for description. It should be noted that the first data collection apparatus 1001 may be disposed on only one foot or both feet of the player. This is not limited herein.

In this embodiment of this application, the first motion data may include foot acceleration data and foot angular velocity data of the player in the motion process. Specifically, the first data collection apparatus 1001 may be an electronic device with an accelerometer and a gyroscope. The electronic device can collect the foot acceleration data and the foot angular velocity data of the player in the motion process.

Figure 2:
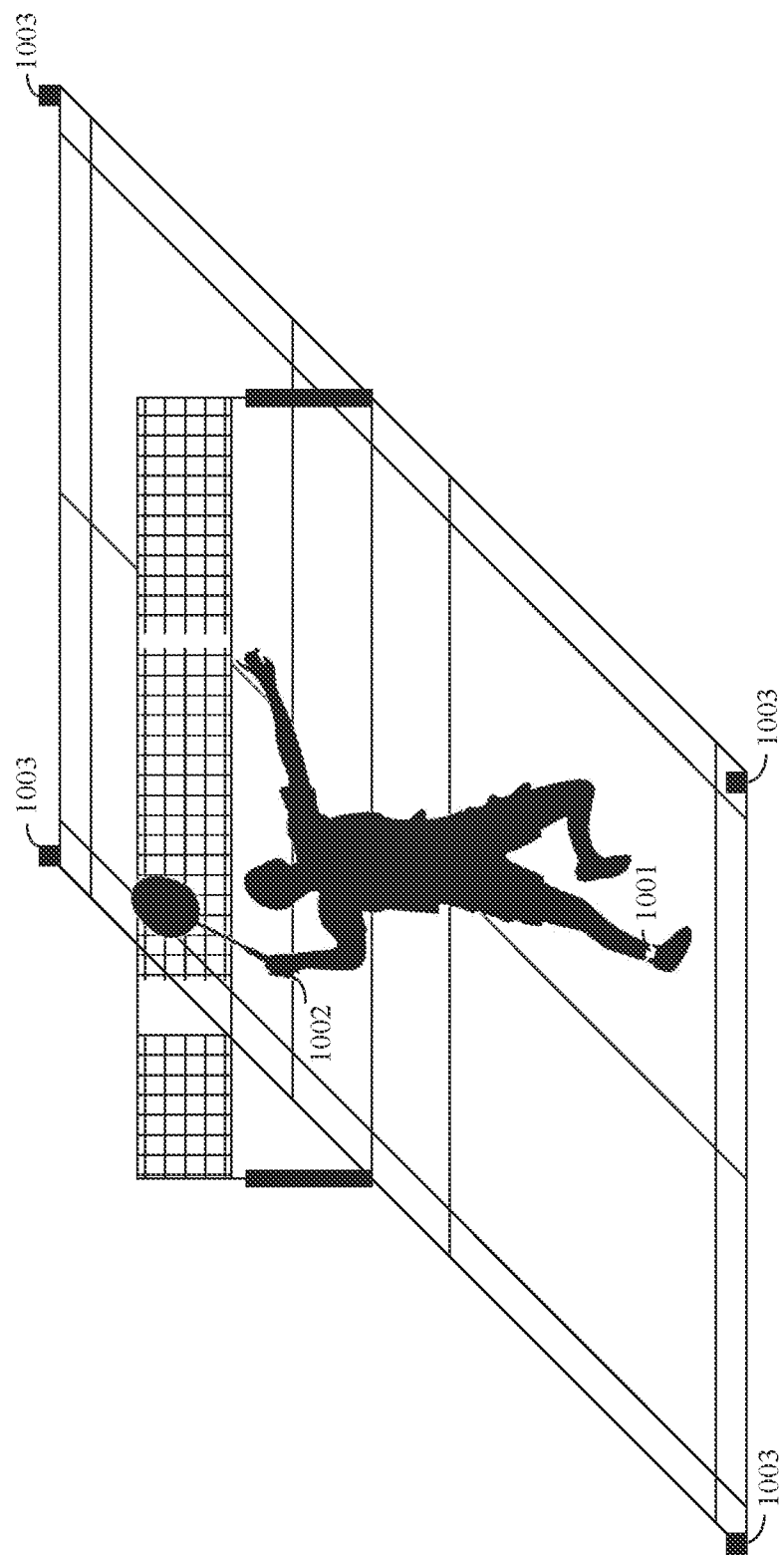
FIG. 2 is a schematic diagram of a usage scenario of the motion monitoring system corresponding to FIG. 1.

Referring to FIG. 2, in a specific application, the first data collection apparatus 1001 may be a wearable device that includes a six-axis inertial sensor. When receiving badminton training, the player can wear, on the ankle, the wearable device including the six-axis inertial sensor. In a training process of the player, the six-axis inertial sensor can collect the foot acceleration data and the foot angular velocity data of the player in the motion process in real time.

Certainly, the first data collection apparatus 1001 may alternatively be a smart shoe. The six-axis inertial sensor is disposed in the smart shoe. After the player wears the smart shoe, the foot acceleration data and the foot angular velocity data of the player in the motion process can be collected in real time by using the six-axis inertial sensor in the smart shoe.

In a specific application, the second data collection apparatus 1002 is configured to collect second motion data. Specifically, the second data collection apparatus may be disposed at a preset location of a racket. The second motion data is motion data that can reflect an upper limb hitting action of the player. The second data collection apparatus 1002 is further configured to send the second motion data collected in real time to the action recognition apparatus 1004 that is communicatively connected to the second data collection apparatus 1002.

In this embodiment of this application, the preset location of the racket may be a racket handle, may be a racket shaft, or may be a racket head. This is not limited herein. In this embodiment of this application, that the preset location of the racket is a racket handle is used as an example for description.

Referring to FIG. 2, the second data collection apparatus 1002 may be embedded in the racket handle. Specifically, the second data collection apparatus 1002 may be embedded on a rear cover of the racket handle. The second motion data that can reflect the upper limb hitting action is collected by using the second data collection apparatus 1002 embedded in the racket handle.

In this embodiment of this application, the second motion data may include hand acceleration data, hand angular velocity data, and acoustic wave data of the player in the motion process. Specifically, the second data collection apparatus 1002 may include an acceleration sensor, a gyroscope, and a microphone. The acceleration sensor is configured to collect the hand acceleration data of the player in the motion process in real time, the gyroscope is configured to collect the hand angular velocity data of the player in the motion process in real time, and the microphone is configured to collect the acoustic wave data of the player in the motion process in real time. Specifically, the second data collection apparatus 1002 may alternatively include a six-axis inertial sensor and a microphone. The six-axis inertial sensor is configured to collect the hand acceleration data and the hand angular velocity data of the player in the motion process in real time The microphone is configured to collect the acoustic wave data of the player in the motion process in real time.

In this embodiment of this application, the third data collection apparatus 1003 is configured to collect third motion data. The third data collection apparatus 1003 may be disposed at a preset shooting location. The third motion data is motion data that can reflect the image action characteristic of the player. The third data collection apparatus 1003 is further configured to send the third motion data collected by the third data collection apparatus 1003 in real time to the action recognition apparatus 1004 that is communicatively connected to the third data collection apparatus 1003.

In this embodiment of this application, the third motion data may be a motion image of the player. The preset shooting location refers to a location in which the motion image of the player can be shot. The preset shooting location can be determined based on an actual requirement. Details are not described herein.

Referring to FIG. 2, in this embodiment of this application, to capture the motion image of the player in all directions, the preset shooting location may be four corners of a court. That is, the motion image of the player in the motion process is collected by using the third data collection apparatus disposed at each of the four corners of the court.

In this embodiment of this application, the third data collection apparatus 1003 may be a terminal device that can collect the motion image of the player, for example, a mobile phone or a camera that has a shooting function. That the third data collection apparatus 1003 is a mobile phone is used as an example. The third motion data is image data or video data shot by the mobile phone.

In this embodiment of this application, the action recognition apparatus 1004 may be a terminal device that has a data processing capability. The action recognition apparatus can process the first motion data collected by the first data collection apparatus 1001, to obtain the gait characteristic of the player in the motion process; can process the second motion data collected by the second data collection apparatus 1002, to obtain the swing gesture characteristic of the player in the motion process; and can further process the third motion data collected by the third data collection apparatus 1003, to obtain the image action characteristic of the player in the motion process. The action recognition apparatus 1004 can further recognize the hitting action of the player in the motion process based on the gait characteristic, the swing gesture characteristic, and the image action characteristic.

In this embodiment of this application, the action recognition apparatus 1004 may be an independent terminal device, for example, may be a wearable device, may be a mobile terminal, for example, a mobile phone, a tablet computer, an augmented reality (augmented reality, AR)/a virtual reality (virtual reality, VR) device, a notebook computer, an ultra-mobile personal computer (ultra-mobile personal computer, UMPC), a netbook, or a personal digital assistant (personal digital assistant, PDA), or may be a server device that has a data processing capability. A specific type of the action recognition apparatus 1004 is not limited in this embodiment of this application. Alternatively, the action recognition apparatus 1004 may be a virtual terminal that has a data processing capability, for example, a virtual computer or a cloud server that does not have a hardware structure.

In this embodiment of this application, alternatively, the action recognition apparatus 1004 and the first data collection apparatus 1001 may be disposed in a same electronic device. In other words, the electronic device may include the first data collection apparatus 1001 and the action recognition apparatus 1004. It may be understood that, alternatively, the action recognition apparatus 1004 and the second data collection apparatus 1002 may be disposed in a same electronic device. In other words, the electronic device may include the second data collection apparatus 1002 and the action recognition apparatus 1004. Similarly, alternatively, the action recognition apparatus 104 and the third data collection apparatus 1003 may be disposed in a same electronic device. In other words, the electronic device may include the third data collection apparatus 1003 and the action recognition apparatus 1004.

Figure 3:
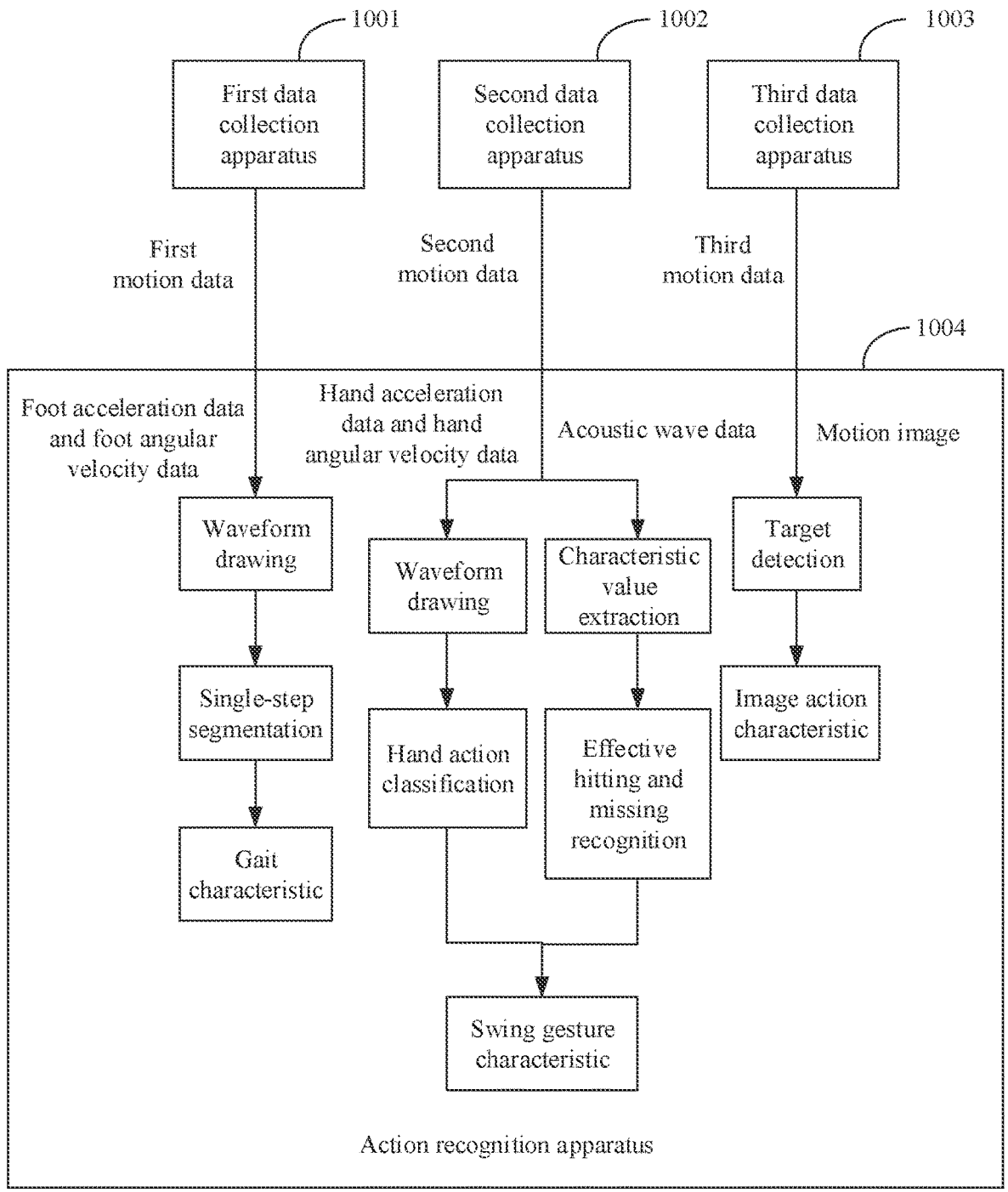
FIG. 3 is a schematic block diagram of a working process of the motion monitoring system corresponding to FIG. 1.

Referring to FIG. 3, in this embodiment of this application, the first data collection apparatus 10001 sends the first motion data collected by the first data collection apparatus 1001 in real time to the action recognition apparatus 1004. After obtaining the first motion data, the action recognition apparatus 1004 can perform single-step segmentation on the first motion data, so as to determine the gait characteristic of the player in the motion process. The gait characteristic of the player in the motion process includes, but is not limited to, a classification of the lower limb action and action parameters of the lower limb action.

In a specific application, the first motion data includes the foot acceleration data and the foot angular velocity data. A process of processing the first motion data specifically includes: drawing a foot acceleration waveform and a foot angular velocity waveform based on the first motion data; determining a departure location and a touchdown location of each step based on the foot acceleration waveform and the foot angular velocity waveform; performing the single-step segmentation on the foot acceleration waveform and the foot angular velocity waveform based on the departure location and the touchdown location of each step; and determining a single-step gait characteristic of the player in the motion process based on a segmented foot acceleration waveform and a segmented foot angular velocity waveform.

Two adjacent peaks in the foot acceleration waveform may represent one action cycle (that is, one step). A time point corresponding to a first peak of the two adjacent peaks is the departure location, a time point corresponding to a second peak is the touchdown location, and a time period between the departure location and the touchdown location is an action cycle. The departure location and the touchdown location of each step can be determined based on the foot acceleration waveform, so as to determine each action cycle, so that the single-step segmentation is performed on a foot acceleration waveform diagram and a foot angular velocity waveform diagram based on the action cycle.

Figure 4:
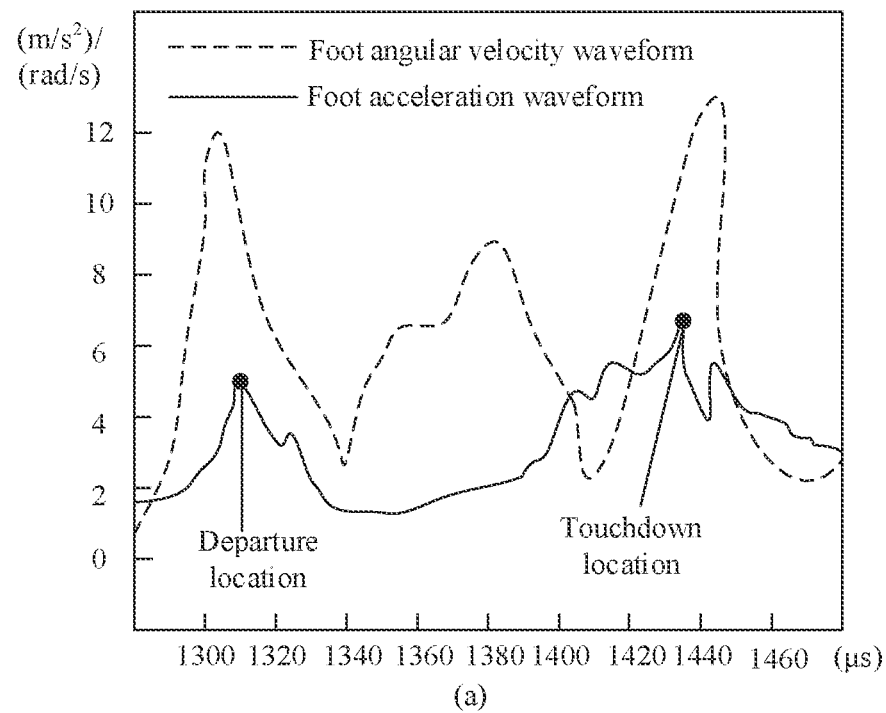
FIG. 4 is a comparison diagram of corresponding foot acceleration waveforms and foot angular velocity waveforms when lower limb actions are respectively walking and jumping.
Figure 4:
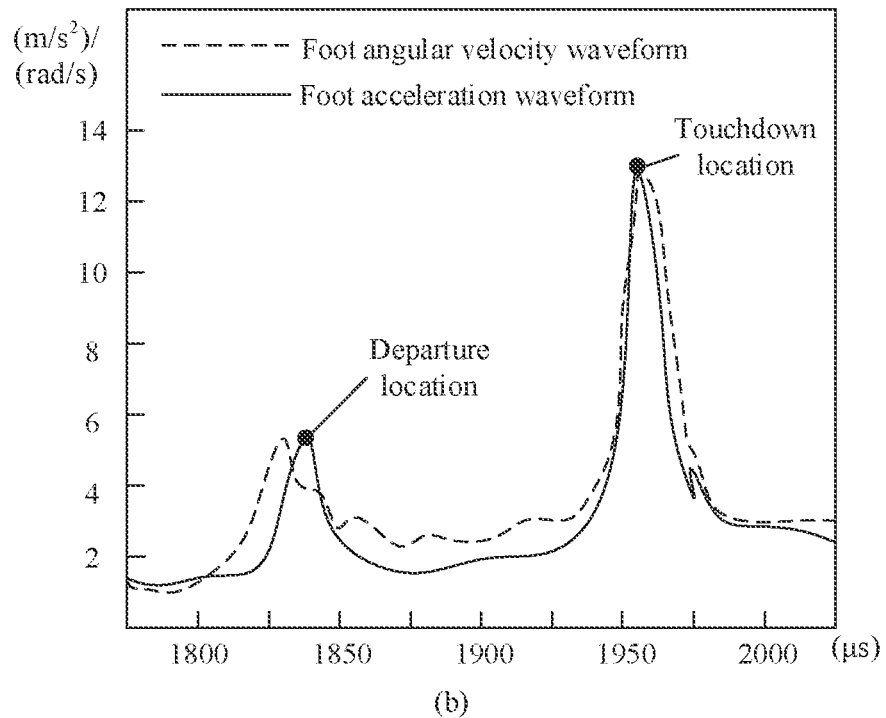

A lower limb action corresponding to each action cycle may be walking, running, jumping, or the like. Different lower limb actions correspond to different foot acceleration waveforms and different foot angular velocity waveforms. Therefore, the lower limb action corresponding to each action cycle can be determined based on the foot acceleration waveform and the foot angular velocity waveform. For example, referring to FIG. 4, when the lower limb action is walking, the foot acceleration waveform and the foot angular velocity waveform are shown in (a) of FIG. 4. When the lower limb action is jumping, the foot acceleration waveform and the foot angular velocity waveform are shown in (b) of FIG. 4. It should be noted that, in FIG. 4, a horizontal coordinate axis indicates a collection time of the first motion data, and a unit is microsecond (μs); and a vertical coordinate axis indicates a value of acceleration and a value of an angular velocity. When the vertical coordinate axis indicates the value of acceleration, a unit is meters per second squared (m/s2). When the vertical coordinate axis indicates the value of an angular velocity, a unit is radians per second (rad/s).

After the lower limb action corresponding to each action cycle is determined, action parameters of the lower limb action corresponding to each action cycle can be further determined based on acceleration, an angular velocity, a departure location, and a touchdown location in each action cycle, for example, a hang duration, a jump height, a moved distance, and a moving speed.

Still referring to FIG. 3, in this embodiment of this application, the second data collection apparatus 1002 can send the second motion data collected by the second data collection apparatus 1002 in real time to the action recognition apparatus 1004 that is communicatively connected to the second data collection apparatus 1002. After obtaining the second motion data, the action recognition apparatus 1004 can process the second motion data, so as to determine the swing gesture characteristic of the player in the motion process. The swing gesture characteristic of the player in the motion process includes, but is not limited to, a type of a hand action, action parameters of the hand action, and whether hitting is effective.

In a specific application, the second motion data may include the hand acceleration data, the hand angular velocity data, and the acoustic wave data. A process of processing the second data specifically includes: drawing a hand acceleration waveform and a hand angular velocity waveform based on the hand acceleration data and the hand angular velocity data; and then determining, based on the hand acceleration waveform and the hand angular velocity waveform, a classification and action parameters of a hand action during each swing. Characteristic values of the acoustic wave data are extracted based on the acoustic wave data, and then effective hitting and missing recognition are performed based on the characteristic values of the acoustic wave data. Finally, based on the classification and the action parameters, determined based on the hand acceleration waveform and the hand angular velocity waveform, of the hand action during each swing, and based on hitting and missing classification performed based on the characteristic values of the acoustic wave data, the swing gesture characteristic of the player during each swing is determined.

Classifications of hand actions during swing include but are not limited to high clear, smash, and chop. The swing action parameters include a hitting speed, hitting power, a hitting trajectory, and the like.

The determining, based on the hand acceleration waveform and the hand angular velocity waveform, a classification of a hand action during each swing and action parameters during swing may be implemented based on an existing classification algorithm model. To be specific, the hand acceleration waveform and the hand angular velocity waveform are input into the existing classification algorithm model for processing, so as to obtain the classification of the hand action during each swing and the action parameters during swing. Details are not described herein again.

The characteristic values of the acoustic wave data include but are not limited to energy, a peak, and a frequency. A time domain waveform of the acoustic wave data only reflects a relationship between a sound pressure and time, but does not reflect the characteristic values of the acoustic wave data. Therefore, the time domain waveform of the acoustic wave data needs to be converted into a frequency domain waveform that can reflect the characteristic values, so that corresponding characteristic values are extracted. Currently, there are many acoustic wave characteristic value extraction methods, such as a method for extracting a characteristic value based on a mel-frequency cepstral coefficient (mel-frequency cepstral coefficients. MFCCs) and a method for extracting a characteristic value based on a linear prediction cepstrum coefficient (linear prediction cepstrum coefficient, LPCC). A process of performing the effective hitting and missing recognition based on the characteristic values of the acoustic wave data specifically includes: performing similarity match calculation on extracted energy, peak, and frequency by using a preset Gaussian mixture model; and when similarity obtained through calculation is greater than a preset threshold, determining that a current hand action is effective hitting; or when the similarity obtained through calculation is less than the preset threshold, determining that the current hand action is missing (namely, noneffective hitting).

The preset Gaussian mixture model is a Gaussian mixture model determined based on historical motion data of each player. Each player has a corresponding preset Gaussian mixture model, and the player can be associated with the preset Gaussian mixture model by using a player ID. The action recognition apparatus 1004 can determine a corresponding preset Gaussian mixture model based on a player ID of a player that currently performs training. The preset Gaussian mixture model is a Gaussian mixture model in which an optimal solution of a Gaussian mixture model parameter is determined, and the Gaussian mixture model parameter may be represented as $\lambda$. A process of solving the optimal solution of $\lambda$ is a training process of the Gaussian mixture model.

In a specific application, to determine the optimal solution of the Gaussian mixture model parameter $\lambda$, N M-dimensional linear weighting functions of Gaussian density functions may be used to represent the Gaussian mixture model, where both N and M are positive integers greater than 1.

A function of the Gaussian mixture model may be represented as:

$$P(X) = \Sigma_{i=1}^{i=N} \omega_i * G_i(X).$$

X is an M-dimensional characteristic parameter of the acoustic wave data, and $X=(X_1, X_2, \ldots, X_M)$; $\omega_i$ refers to a weight of an $i^{th}$ Gaussian density function, and $\Sigma_{i=1}^{i=N} \omega_i = 1$; and $G_i(X)$ is a Gaussian probability-density function of the characteristic parameter X.

$$G_i(X) = \frac{1}{(2\pi)^{\frac{M}{2}} |C_i|^{\frac{1}{2}}} \exp\left\{-\frac{1}{2}(X-\mu_i)^T C_i^{-1}(X-\mu_i)\right\}.$$

$C_i$ refers to a covariance matrix of the $i^{th}$ Gaussian density function, and $\mu_i$ refers to a mean vector of the $i^{th}$ Gaussian density function.

$C_i$ refers to a covariance matrix of the $i^{th}$ Gaussian density function, and $\mu_i$ refers to a mean vector of the $i^{th}$ Gaussian density function.

Specifically, the optimal solution of $\lambda$ may be estimated based on iterative calculation of an expectation maximization algorithm by using $\lambda=(\omega_i, \mu_i, C_i)$.

After it is determined whether effective hitting or missing is performed when the player swings, the swing gesture characteristic can be determined with reference to the classification of the hand action during each swing. For example, it is assumed that classifications, determined based on the hand acceleration data and the hand angular velocity data, of hand actions of the player in the motion process are as follows: A first hand action is high clear, a second hand action is smash, and a third hand action is chop. Based on the acoustic wave data, it is determined that the first hand action is missing, the second hand action is effective hitting, and the third hand action is effective hitting. Then swing gesture characteristics of the player in the motion process can be determined as follows: The first hand action is noneffective high clear, and a hitting speed, hitting power, a hitting trajectory, and the like during hitting are determined; the second hand action is effective smash, and a hitting speed, hitting power, a hitting trajectory, and the like during hitting are determined; and the third hand action is effective chop, and a hitting speed, hitting power, a hitting trajectory, and the like during hitting are determined.

Still referring to FIG. 3, in this embodiment of this application, the third data collection apparatus 1003 can send the third motion data collected by the third data collection apparatus 1003 in real time to the action recognition apparatus 1004 that is communicatively connected to the third data collection apparatus 1003. After obtaining the third motion data, the action recognition apparatus 1004 can analyze the image action characteristic of the player in the motion process based on the third motion data and a convolutional neural network model.

In this embodiment of this application, the third motion data is a motion image of the player. When processing the third motion data, the action recognition apparatus 1004 can first perform target detection, select, from the motion image, a target image region that includes the player, and then recognize a leg curl characteristic of the player in an image based on the image in the target image region. In this way, when the action recognition apparatus 1004 uses the convolutional neural network model to process the motion image, an operation amount can be effectively reduced, occupation of calculation resources can be reduced, and processing efficiency can be improved.

The image action characteristic includes, but is not limited to, the leg curl characteristic (there is leg curl and there is no leg curl) of the player in the image.

The convolutional neural network model refers to a convolutional neural network model that has been trained and that can be used to process the third motion data to determine the image action characteristic. The convolutional neural network model used for image processing may use an existing convolutional neural network model. In a process of training the convolutional neural network model, a large quantity of motion images of a known classification can be used to train the convolutional neural network model, so that when the third motion data is input, the image action characteristic corresponding to the third motion data can be input into the trained convolutional neural network model. For a process of constructing and training the convolutional neural network model, refer to an existing construction and training method. Details are not described herein in this embodiment of this application again.

The trained convolutional neural network model may be stored in a data storage region of the action recognition apparatus 1004. After receiving the third motion data collected by the third data collection apparatus 1003, the action recognition apparatus 1004 automatically invokes the convolutional neural network model to process the third motion data, to obtain the image action characteristic corresponding to the third motion data.

It may be understood that the image action characteristic may further include the classification of the hitting action, that is, the convolutional neural network model can further determine the classification of the hitting action of the player based on the input motion image. Then, with reference to the gait characteristic determined by using the first motion data and the swing gesture characteristic determined by using the second motion data, the hitting action of the player and parameters of the hitting action are comprehensively determined.

Still referring to FIG. 3, in this embodiment of this application, after obtaining the gait characteristic, the swing gesture characteristic, and the image action characteristic, the action recognition apparatus 1004 can finally determine the hitting action of the player in the motion process by combining these characteristics (namely, the gait characteristic, the swing gesture characteristic, and the image action characteristic). In addition, action parameters such as a hitting speed, hitting power, a hang duration, a jump height, a moved distance, and a moving speed of the player during hitting in the motion process can also be determined.

In this embodiment of this application, hitting actions of the player may include effective high clear, effective jump smash with leg curl, effective jump smash without leg curl, effective in-situ smash, effective chop, noneffective high clear, noneffective jump smash, noneffective in-situ smash, noneffective chop, and the like.

The finally determining the hitting action of the player in the motion process by combining the gait characteristic, the swing gesture characteristic, and the image action characteristic may include: combining the gait characteristic, the swing gesture characteristic, and the image action characteristic first, so as to determine the hitting action of the player during hitting; then determining a leg curl angle when leg curl appears when the player jumps; correcting the jump height of the player based on the hang duration and the leg curl angle, and finally recognizing the hitting action of the player in the motion process and action parameters corresponding to each hitting action.

For example, it is assumed that lower limb actions, determined based on the first motion data collected by the first data collection apparatus 1001, of the player in the motion process are respectively walking, jumping, and jumping, types of hand actions that are determined based on the second motion data collected by the second data collection apparatus 1002 are respectively effective chop, noneffective smash, and effective smash, and leg curl characteristics determined based on the third motion data collected by the third data collection apparatus 1003 are respectively that there is no leg curl, there is no leg curl, and there is leg curl. These characteristics are combined to determine that hitting actions of the player in the motion process are respectively effective chop, noneffective jump smash, and effective jump smash with leg curl.

In this embodiment of this application, an action image corresponding to a jump action is obtained only when the jump action is detected, and then whether the player has leg curl is recognized based on the action image. If there is leg curl, a jump height is corrected with reference to a leg curl angle and a hang duration. If there is no leg curl in the jump action of the player, correction does not need to be performed. It should be noted that correction of the jump height may be implemented based on an existing correction model. Details are not described herein again.

In conclusion, comprehensive and accurate analysis of the hitting action of the player in the motion process can be implemented, and the action parameters corresponding to each hitting action can be determined. This is conducive to performing comprehensive analysis on the comprehensive sports capability of the player, and is more helpful to formulating the personalized training plan for the player.

Figure 5:
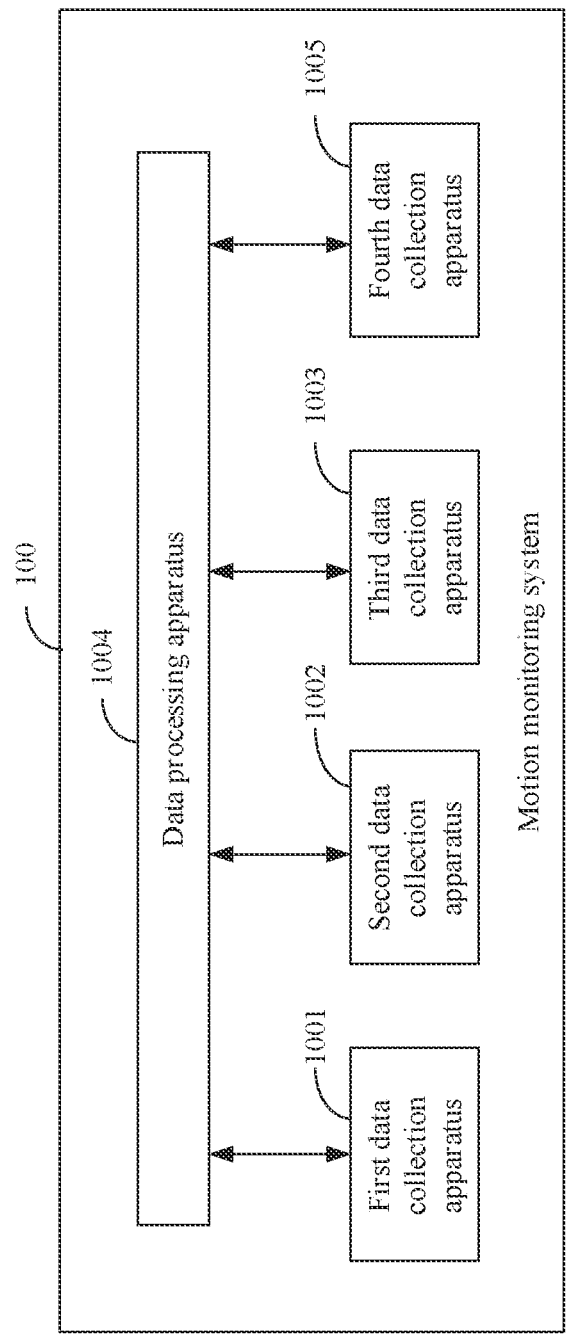
FIG. 5 is a schematic diagram of an architecture of another motion monitoring system according to an embodiment of this application.

FIG. 5 is a block diagram of a structure of another motion monitoring system according to an embodiment of this application. As shown in FIG. 5, different from the foregoing embodiment of this application, the motion monitoring system further includes a fourth data collection apparatus 1005. The fourth data collection apparatus 1005 is also communicatively connected to the action recognition apparatus 1004.

The action recognition apparatus 1004 can establish a wireless communication connection to the fourth data collection apparatus 1005 in a short-range communication connection manner, or the action recognition apparatus 1004 can establish a wired communication connection to the fourth data collection apparatus 1005 in a wired communication manner. A specific communication manner between the action recognition apparatus 1004 and the fourth data collection apparatus 1005 is not limited in this embodiment of this application.

The short-range communication connection manner may be a Bluetooth connection, a near field communication (Near Field Communication, NFC) connection, a wireless-fidelity (Wireless-Fidelity, Wi-Fi) connection, a ZigBee (ZigBee) connection, or the like. To improve convenience of use of the player, a Bluetooth connection may be preferably used in this embodiment. A short-range communication identifier is a unique identifier related to a short-range communication connection of a terminal device. If the Bluetooth connection is used, the short-range communication identifier may be correspondingly a Bluetooth media access control (Media Access Control, MAC) address or another unique identifier of a Bluetooth device.

The fourth data collection apparatus 1005 is configured to collect fourth motion data. The fourth data collection apparatus may be disposed at a second preset part of the player. The fourth motion data is motion data that can reflect physiological parameters of the player in the motion process. The physiological parameters include but are not limited to a heart rate, a pulse, and a body temperature. In this embodiment of this application, the fourth motion data includes, but is not limited to, heart rate data of the player in the motion process.

In this embodiment of this application, the second preset part of the player refers to a part in which the fourth motion data can be collected, for example, a wrist of the player. Certainly, the second preset part of the player may alternatively be another part in which the fourth motion data can be collected, for example, a fingertip or a neck. This is not limited herein.

Figure 6:
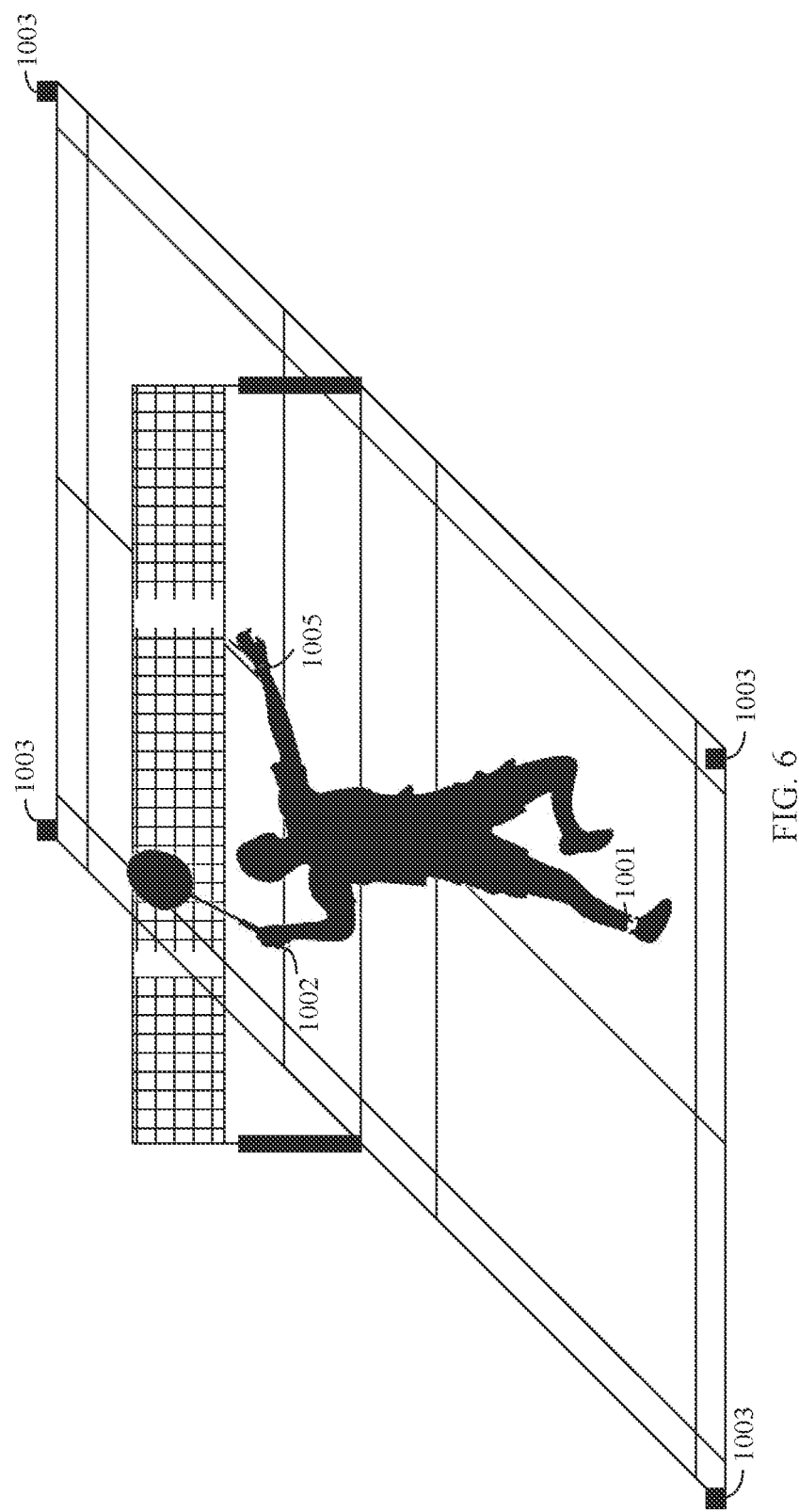
FIG. 6 is a schematic diagram of a usage scenario of the motion monitoring system corresponding to FIG. 5.

Referring to FIG. 6, in a specific application, the fourth data collection apparatus 1005 may be a wearable device that can collect the heart rate data, for example, a smart watch or a smart bracelet. When receiving badminton training, the player can wear the wearable device on the wrist. In the training process of the player, the wearable device can collect the heart rate data of the player in the motion process in real time.

In an actual application, the wearable device may include a photoplethysmograph (photoplethysmograph, PPG) sensor configured to collect the heart rate data, where the heart rate data at the wrist of the player is collected by using the PPG sensor.

Figure 7:
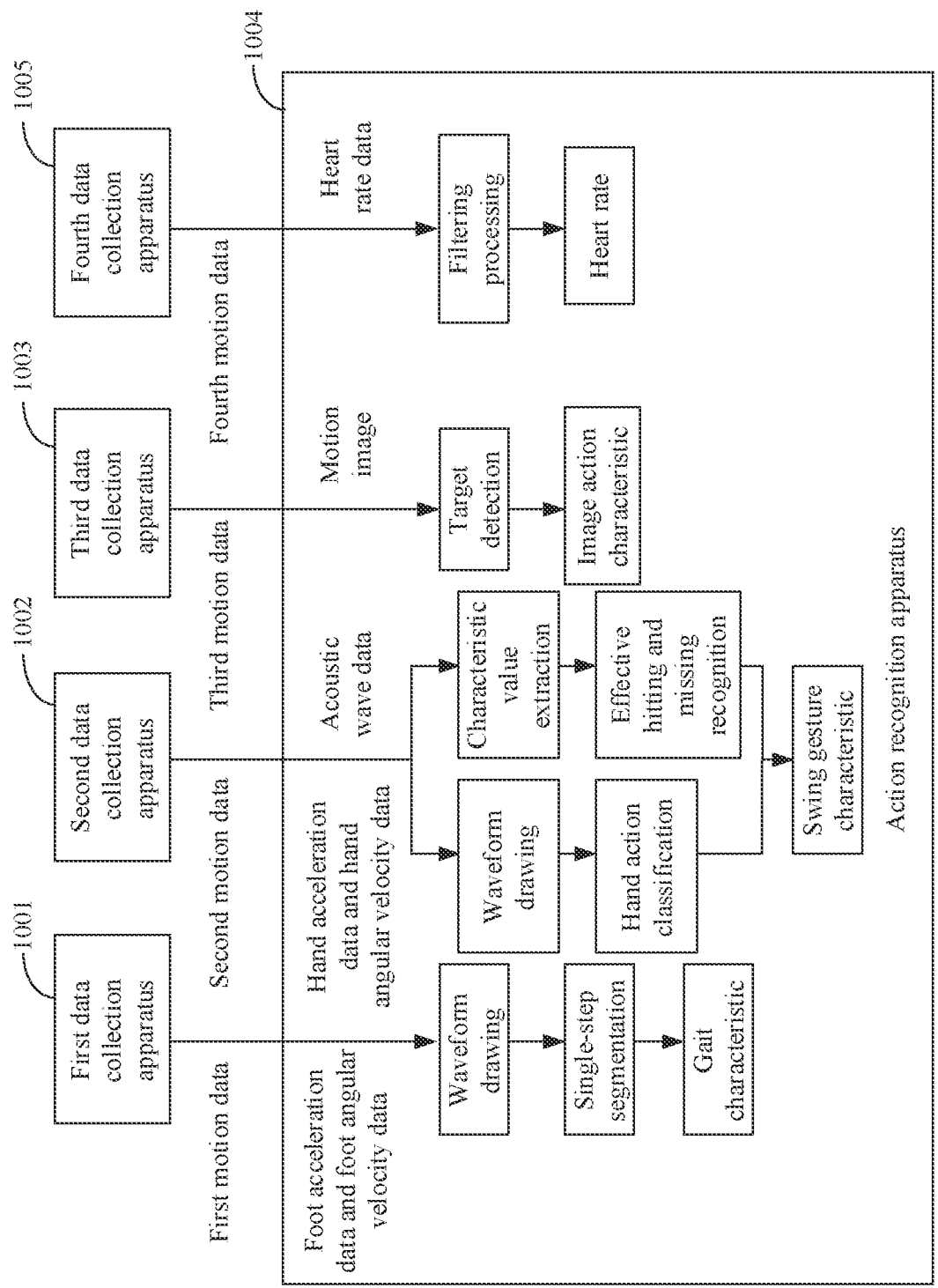
FIG. 7 is a schematic block diagram of a working process of the motion monitoring system corresponding to FIG. 5.

Also referring to FIG. 7, in this embodiment of this application, the action recognition apparatus 1004 can further process the fourth motion data collected by the fourth data collection apparatus 1005, so as to determine the heart rate of the player in the motion process.

The fourth motion data may be PPG data collected based on the photoplethysmograph (photoplethysmograph, PPG) sensor. Specifically, the action recognition apparatus 1004 can perform filtering processing on the fourth motion data, so as to determine the heart rate of the player in the motion process.

It should be noted that when the fourth motion data is pulse data, the action recognition apparatus can perform pulse waveform peak interval characteristic extraction processing on the pulse data, so as to determine a heart rate value of the player in the motion process.

In this embodiment of this application, after determining, based on the first motion data, the second motion data, and the third motion data, the hitting action of the player in the motion process and the action parameters corresponding to each hitting action, the action recognition apparatus can further analyze motion intensity and a physical capability of the player based on the heart rate determined based on the fourth motion data. Therefore, more comprehensive evaluation can be performed on the comprehensive sports capability of the player.

For ease of understanding, the following describes in detail an action recognition process.

Figure 8:
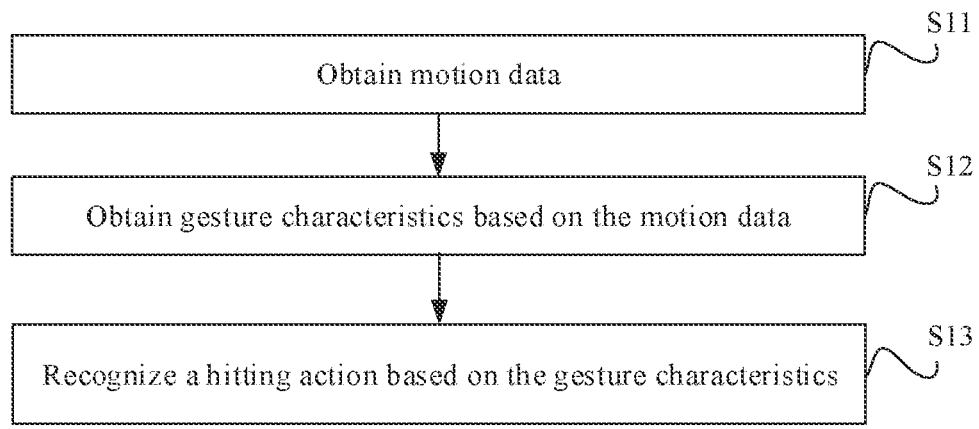
FIG. 8 is a schematic flowchart of implementing an action method according to an embodiment of this application.

FIG. 8 is a schematic flowchart of an action recognition method according to an embodiment of this application. The action recognition method may be performed by the action recognition apparatus in the foregoing embodiments. As shown in FIG. 8, the method may include the following steps:

S11: Obtain motion data.

Herein, to recognize a hitting action of a player in a motion process, the motion data of the player in the motion process needs to be first obtained. In this embodiment of this application, the motion data includes first motion data, second motion data, and third motion data.

The first motion data is motion data that can reflect a lower limb action of the player in the motion process. The second motion data is motion data that can reflect an upper limb hitting action of the player in the motion process. The third motion data is motion data that can reflect an image action characteristic of the player.

In this embodiment of this application, the first motion data may include foot acceleration data and foot angular velocity data of the player in the motion process. The second motion data may include hand acceleration data, hand angular velocity data, and acoustic wave data of the player in the motion process. The third motion data may include a motion image of the player.

The first motion data is collected by a first data collection apparatus located at a first preset part of the player; the second motion data is collected by a second data collection apparatus disposed at a preset location of a racket; and the third motion data is collected by a third data collection apparatus disposed at a preset shooting location.

The first preset part of the player may be a lower leg or thigh location of the player, may be an ankle of the player, or may be another preset part in which the motion data of the lower limb action of the player can be collected.

The preset location of the racket may be a racket handle, may be a racket shaft, or may be a racket head. This is not limited herein.

The preset shooting location refers to a location in which the motion image of the player can be shot. The preset shooting location can be determined based on an actual requirement. Details are not described herein.

In this embodiment of this application, each data collection apparatus can store, in a local memory of the data collection apparatus, motion data collected in real time. Based on this, when the action recognition apparatus needs to obtain the motion data, each data collection apparatus can send the motion data stored in the local memory to the action recognition apparatus that is communicatively connected to the data collection apparatus.

S12: Obtain gesture characteristics based on the motion data.

In this embodiment of this application, the obtaining gesture characteristics based on the motion data includes: obtaining a gait characteristic of the player in the motion process based on the first motion data; obtaining a swing gesture characteristic of the player in the motion process based on the second motion data; and obtaining an image action characteristic of the player in the motion process based on the third motion data.

In this embodiment of this application, the first motion data includes the foot acceleration data and the foot angular velocity data. A process of obtaining the gait characteristic of the player in the motion process based on the first motion data specifically includes: drawing a foot acceleration waveform and a foot angular velocity waveform based on the first motion data; determining a departure location and a touchdown location of each step based on the foot acceleration waveform and the foot angular velocity waveform; performing single-step segmentation on the foot acceleration waveform and the foot angular velocity waveform based on the departure location and the touchdown location of each step; and determining the gait characteristic of the player in the motion process based on a segmented foot acceleration waveform and a segmented foot angular velocity waveform.

The gait characteristic of the player in the motion process includes, but is not limited to, a classification of the lower limb action and action parameters of the lower limb action. Classifications of lower limb actions may be walking, running, jumping, and the like. The action parameters of the lower limb action may be a hang duration, a jump height, a moved distance, a moving speed, and the like.

In this embodiment of this application, the second motion data may include the hand acceleration data, the hand angular velocity data, and the acoustic wave data. A process of obtaining the swing gesture characteristic of the player in the motion process based on the second motion data specifically includes: drawing a hand acceleration waveform and a hand angular velocity waveform based on the hand acceleration data and the hand angular velocity data, and then determining, based on the hand acceleration waveform and the hand angular velocity waveform, a classification and action parameters of a hand action during each swing; extracting characteristic values of the acoustic wave data based on the acoustic wave data, and then performing effective hitting and missing recognition based on the characteristic values of the acoustic wave data; and based on the classification and the action parameters, determined based on the hand acceleration waveform and the hand angular velocity waveform, of the hand action during each swing, and based on effective hitting and missing classification performed based on the characteristic values of the acoustic wave data, finally determining the swing gesture characteristic of the player during each swing.

The swing gesture characteristic of the player in the motion process includes, but is not limited to, a type of the hand action, the action parameters of the hand action, and whether hitting is effective.

Classifications of hand actions during swing include but are not limited to high clear, smash, and chop. The swing action parameters include a hitting speed, hitting power, a hitting trajectory, and the like.

In this embodiment of this application, the third motion data may include the motion image of the player. A process of obtaining the image action characteristic of the player in the motion process based on the third motion data specifically includes: first performing target detection on the motion image, selecting, from the motion image, a target image region that includes the player, and then inputting the target image region into a trained convolutional neural network model for processing, so as to determine the image action characteristic of the player in the motion process.

The image action characteristic includes, but is not limited to, a leg curl characteristic (there is leg curl and there is no leg curl) of the player in the image.

It may be understood that the third motion data may further be an image that includes a court heat map or the like that can be used to draw motion trajectory distribution (a motion trajectory of the player, a motion trajectory of a ball, and the like) on a court. The court heat map can be used to assist in analyzing a gait characteristic during motion, locations in which a point is won and a point is lost, and the like.

S13: Recognize a hitting action based on the gesture characteristics.

In this embodiment of this application, after the gait characteristic, the swing gesture characteristic, and the image action characteristic are obtained, the gait characteristic, the swing gesture characteristic, and the image action characteristic are combined to finally recognize the hitting action of the player in the motion process.

The finally determining the hitting action of the player in the motion process by combining the gait characteristic, the swing gesture characteristic, and the image action characteristic may include: combining the gait characteristic, the swing gesture characteristic, and the image action characteristic first, so as to determine the hitting action of the player during hitting; then determining a leg curl angle when leg curl appears when the player jumps; correcting the jump height of the player based on the hang duration and the leg curl angle; and finally recognizing the hitting action of the player in the motion process and action parameters corresponding to each hitting action.

For example, determined gait characteristics of the player in the motion process are respectively walking, jumping, and jumping; swing gesture characteristics of the player in the motion process are effective chop, noneffective smash, and effective smash; and image action characteristics are respectively that there is no leg curl, there is no leg curl, and there is leg curl. These characteristics are combined to determine that hitting actions of the player in the motion process are respectively effective chop, noneffective jump smash, and effective jump smash with leg curl.

In another embodiment of this application, the action parameters of the hitting action may be further obtained based on the motion data.

In this embodiment of this application, the action parameters of the hitting action may include a hitting speed, hitting power, a hang duration, a jump height, a moved distance, a moving speed, and the like. For a process of obtaining the action parameters, refer to the foregoing embodiments. Details are not described herein again. By determining the action parameters of the player during hitting, more specific analysis can be performed on a comprehensive sports capability of the player.

In another embodiment of this application, when the hitting action is effective smash with leg curl, the jump height of the player is corrected based on the hang duration and the leg curl angle. Then the comprehensive sports capability of the player is analyzed based on a corrected jump height. For a process of correcting the jump height, refer to the foregoing embodiments. Details are not described herein again. The jump height of the player is corrected, so that motion parameters of the player can be more accurately measured.

In another embodiment of this application, the motion data may further include fourth motion data. Physiological parameters of the player in the motion process can be determined based on the fourth motion data.

In a specific application, the fourth motion data is collected by a fourth data collection apparatus disposed at a second preset part of the player. The fourth motion data is motion data that can reflect the physiological parameters of the player in the motion process. The physiological parameters include but are not limited to a heart rate, a pulse, and a body temperature.

In this embodiment of this application, the fourth motion data includes, but is not limited to, heart rate data of the player in the motion process.

In this embodiment of this application, the second preset part of the player refers to a part in which the fourth motion data can be collected, for example, a wrist of the player. Certainly, the second preset part of the player may alternatively be another part in which the fourth motion data can be collected, for example, a fingertip or a neck. This is not limited herein.

Specifically, the heart rate data is filtered to determine the heart rate of the player in the motion process. For a process of performing filtering processing on the heart rate data to determine the heart rate, refer to an existing method for processing heart rate data. Details are not described herein again.

According to the action recognition method provided in this embodiment, characteristic extraction and action recognition can be performed based on the motion data collected by the data collection apparatuses; a gait characteristic, a swing gesture characteristic, and an image action characteristic of a user are recognized by using a plurality of pieces of motion data; and a type of the hitting action of the player is determined based on the gait characteristic, the swing gesture characteristic, and the image action characteristic. In this way, the hitting action of the player in the motion process can be accurately recognized. This is conducive to performing comprehensive analysis on the comprehensive sports capability of the player, and is more helpful to formulating a personalized training plan for the player.

Figure 9:
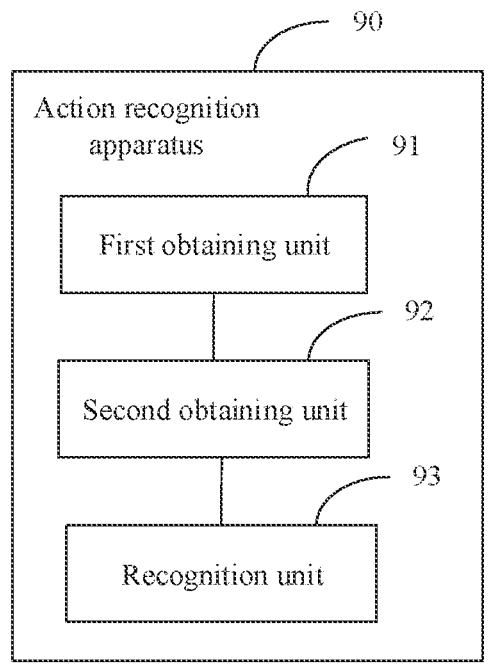
FIG. 9 is a schematic diagram of a structure of an action recognition apparatus according to an embodiment of this application.

Corresponding to the action recognition method described in the foregoing embodiment, FIG. 9 is a block diagram of a structure of an action recognition apparatus according to an embodiment of this application. Units included in the action recognition apparatus are configured to perform the steps in the foregoing embodiment. For details, refer to related descriptions in the foregoing embodiment. For ease of description, only parts related to the embodiments of this application are shown. Referring to FIG. 9, the action recognition apparatus 90 includes a first obtaining unit 91, a second obtaining unit 92, and a recognition unit 93.

The first obtaining unit 91 is configured to obtain motion data.

The motion data includes first motion data, second motion data, and third motion data.

The second obtaining unit 92 is configured to obtain gesture characteristics based on the motion data.

The second obtaining unit 92 is specifically configured to: obtain a gait characteristic of a player in a motion process based on the first motion data, obtain a swing gesture characteristic of the player in the motion process based on the second motion data, and obtain an image action characteristic of the player in the motion process based on the third motion data The recognition unit 93 is configured to recognize a hitting action based on the gesture characteristics.

The recognition unit 93 is specifically configured to recognize the hitting action of the player in the motion process based on the gait characteristic, the swing gesture characteristic, and the image action characteristic.

In an embodiment of this application, the action recognition apparatus further includes a third obtaining unit, where the third obtaining unit is configured to obtain action parameters of the hitting action based on the motion data.

In this embodiment of this application, the first obtaining unit is further configured to obtain fourth motion data. Correspondingly, the action recognition apparatus further includes a physiological parameter determining unit, where the physiological parameter determining unit is configured to determine physiological parameters of the player in the motion process based on the fourth motion data.

In an embodiment of this application, the action recognition apparatus further includes a correction unit, where the correction unit is configured to: when the hitting action is effective smash with leg curl, correct a jump height of the player based on a hang duration and a leg curl angle.

It can be learned from the foregoing that, in the action recognition apparatus provided in this embodiment of this application, characteristic extraction and action recognition can also be performed based on the motion data collected by the data collection apparatuses; a gait characteristic, a swing gesture characteristic, and an image action characteristic of a user are recognized by using a plurality of pieces of motion data; and a type of the hitting action of the player is determined based on the gait characteristic, the swing gesture characteristic, and the image action characteristic. In this way, the hitting action of the player in the motion process can be accurately recognized. This is conducive to performing comprehensive analysis on a comprehensive sports capability of the player, and is more helpful to formulating a personalized training plan for the player.

Figure 10:
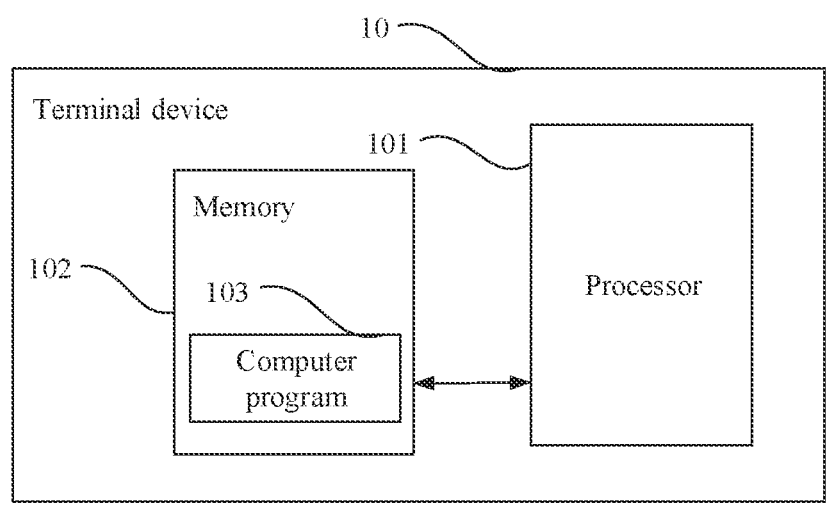
FIG. 10 is a schematic diagram of a structure of a terminal device according to an embodiment of this application.

FIG. 10 is a schematic diagram of a structure of a terminal device according to another embodiment of this application. As shown in FIG. 10, the terminal device 10 in this embodiment includes at least one processor 101 (only one is shown in FIG. 10), a memory 102, and a computer program 103 that is stored in the memory 102 and that can run on the at least one processor 101, where w % ben the processor 101 executes the computer program 103, the steps in any one of the foregoing action recognition method embodiments are implemented.

The terminal device 10 may be a computing device, for example, a desktop computer, a notebook computer, a palm-top computer, or a cloud server. The terminal device may include, but is not limited to, a processor 101 and a memory 102. A person skilled in the art may understand that FIG. 10 is merely an example of the terminal device 10, and does not constitute a limitation on the terminal device 10. The terminal device 10 may include more or fewer components than those shown in the figure, or may combine some components or different components, for example, may further include an input/output device, a network access device, and the like.

The processor 101 may be a central processing unit (Central Processing Unit, CPU). The processor 101 may alternatively be another general-purpose processor, a digital signal processor (Digital Signal Processor, DSP), an application-specific integrated circuit (Application-Specific Integrated Circuit, ASIC), a field-programmable gate array (Field-Programmable Gate Array, FPGA) or another programmable logic device, a discrete gate or a transistor logic device, a discrete hardware component, or the like. The general-purpose processor may be a microprocessor, or the processor may be any conventional processor or the like.

In some embodiments, the memory 102 may be an internal storage unit of the terminal device 10, for example, a hard disk or a memory of the terminal device 10. In some other embodiments, the memory 102 may alternatively be an external storage device of the terminal device 10, for example, a plug-in hard disk, a smart media card (Smart Media Card, SMC), a secure digital (Secure Digital, SD) card, or a flash card (Flash Card) that is configured on the terminal device 10. Further, the memory 102 may alternatively include both the internal storage unit and the external storage device of the terminal device 100. The memory 102 is configured to store an operating system, an application, a boot loader (Boot Loader), data, and another program, for example, program code of the computer program. The memory 102 may be further configured to temporarily store data that has been or is to be output. In this embodiment of this application, the memory 102 may further store an action recognition algorithm library determined based on the action recognition method provided in the embodiments of this application.

It should be noted that content such as information interaction and an execution process between the apparatuses/units is based on a same concept as that in the method embodiments of this application. Therefore, for specific functions and technical effects brought by the apparatuses/units, refer to the method embodiment parts. Details are not described herein again.

A person skilled in the art may clearly understand that, for ease and brevity of description, division of the foregoing functional units and modules is merely used as an example for description. In an actual application, the foregoing functions may be allocated to different functional units and modules based on a requirement, that is, an internal structure of an apparatus is divided into different functional units or modules, to complete all or some of the functions described above. The functional units and modules in the embodiments may be integrated into one processing unit, each unit may separately physically exist, or two or more units may be integrated into one unit. The integrated unit may be implemented in a form of hardware or in a form of a software functional unit. In addition, specific names of the functional units and modules are also used for ease of mutual distinction, and are not used to limit the protection scope of this application. For a specific working process of each of the units and the modules in the foregoing system, refer to a corresponding process in the foregoing method embodiments. Details are not described herein again.

An embodiment of this application further provides a computer-readable storage medium, where the computer-readable storage medium stores a computer program, and when the computer program is executed by a processor, the steps in the action recognition method may be implemented.

An embodiment of this application provides a computer program product, where when the computer program product runs on a mobile terminal, the mobile terminal is enabled to perform the steps in the action recognition method.

In addition, an embodiment of this application further provides an apparatus. The apparatus may specifically be a chip, a component, or a module. The apparatus may include a processor and a memory that are connected, where the memory is configured to store computer execution instructions, and when the apparatus operates, the processor may execute the computer execution instructions stored in the memory, so that the chip performs the interaction method in the foregoing method embodiments.

If an integrated unit is implemented in a form of a software functional unit and sold or used as an independent product, the integrated unit may be stored in a computer-readable storage medium. Based on such an understanding, in this application, a procedure of the embodiment method may be completely or partially implemented by instructing related hardware by using a computer program. The computer program may be stored in a computer-readable storage medium, and when the computer program is executed by a processor, the steps in the foregoing method embodiments can be implemented. The computer program includes computer program code, and the computer program code may be in a source code form or an object code form, may be an executable file, may be in some intermediate forms, or the like. The computer-readable medium may include at least any entity or apparatus that can carry computer program code to a shooting apparatus/terminal device, a recording medium, a computer memory, a read-only memory (Read-Only Memory, ROM), a random access memory (Random Access Memory, RAM), an electrical carrier signal, a telecommunications signal, and a software distribution medium. For example, the computer-readable medium may include a USB flash drive, a removable hard disk, a magnetic disk, or an optical disc. In some jurisdictions, according to legislation and patent practice, the computer-readable medium cannot be an electrical carrier signal or a telecommunications signal.

In the foregoing embodiments, descriptions of each embodiment are particularly emphasized. For a part that is not described or recorded in detail in an embodiment, refer to related descriptions in another embodiment.

A person of ordinary skill in the art may recognize that the units and algorithm steps of the examples described with reference to embodiments disclosed herein can be implemented by using electronic hardware or a combination of computer software and electronic hardware. Whether these functions are implemented in a hardware or software manner depends on a specific application and a design constraint of a technical solution. A person skilled in the art may use different methods to implement described functions in each specific application. However, this implementation should not be considered beyond the scope of this application.

In the embodiments provided in this application, it should be understood that the disclosed apparatus/network device and method may be implemented in another manner. For example, the described apparatus/network device embodiment is merely an example. For example, division of the modules or units is merely logical function division. In an actual implementation, there may be another division manner. For example, a plurality of units or components may be combined or integrated into another system, or some characteristics may be ignored or not performed. In addition, the displayed or discussed mutual coupling, direct coupling, or communication connection may be implemented by using some interfaces, and indirect coupling or communication connection between apparatuses or units may be in an electrical, mechanical, or another form.

The units described as separate components may or may not be physically separated, and components displayed as units may or may not be physical units, that is, may be located at one place, or may be separately located on a plurality of network units. Some or all of the units may be selected based on an actual requirement to implement the objectives of the solutions in the embodiments.

The foregoing embodiments are merely used to describe the technical solutions of this application, but not for limiting this application. Although this application is described in detail with reference to the foregoing embodiments, a person of ordinary skill in the art should understand that the technical solutions described in the foregoing embodiments may still be modified, or some technical characteristics thereof may be equivalently replaced. In addition, these modifications or replacements do not enable the essence of corresponding technical solutions to deviate from the spirit and scope of the technical solutions of embodiments of this application, and should all fall within the protection scope of this application.

What is claimed is:

1. An action recognition method performed by an action recognition apparatus, comprising:
   obtaining motion data through a short-range communication connection, wherein the short-range communication connection is at least one of a Bluetooth connection, a near field communication (NFC) connection, a wireless-fidelity (Wi-Fi) connection, or a ZigBee connection, and wherein the motion data comprises first motion data, second motion data, and third motion data, the first motion data is collected by a first data collection apparatus located at a first preset part of a player, the second motion data is collected by a second data collection apparatus disposed at a preset location of a racket, and the third motion data is collected by a third data collection apparatus disposed at a preset shooting location;
   obtaining a gait characteristic of the player in a motion process based on the first motion data;
   obtaining a swing gesture characteristic of the player in the motion process based on the second motion data;
   obtaining an image action characteristic of the player in the motion process based on using a trained convolutional neural network model to process the third motion data;
   recognizing a hitting action of the player in the motion process based on the gait characteristic, the swing gesture characteristic, and the image action characteristic; and
   when it is recognized that the hitting action is an effective smash with leg curl:
      obtaining a leg curl angle, a hang duration, and a jump height; and
      correcting the jump height based on the hang duration and the leg curl angle.

2. The action recognition method according to claim 1, wherein the first motion data comprises foot acceleration data and foot angular velocity data, and the obtaining a gait characteristic of the player in a motion process based on the first motion data comprises:
   drawing a foot acceleration waveform and a foot angular velocity waveform based on the foot acceleration data and the foot angular velocity data, and extracting a foot acceleration waveform characteristic;
   determining a departure location and a touchdown location of each step based on the foot acceleration waveform characteristic;
   performing single-step segmentation on the foot acceleration waveform and the foot angular velocity waveform based on the departure location and the touchdown location of each step; and
   determining, based on a segmented foot acceleration waveform and a segmented foot angular velocity waveform, a classification of a lower limb action corresponding to each step of the player and action parameters of the lower limb action.

3. The action recognition method according to claim 1, wherein the second motion data comprises hand acceleration data, hand angular velocity data, and acoustic wave data, and the obtaining a swing gesture characteristic of the player in the motion process based on the second motion data comprises:
   determining a classification of a hand action of the player in the motion process and action parameters of the hand action based on the hand acceleration data and the hand angular velocity data;
   performing effective hitting and missing recognition on each hand action of the player in the motion process based on the acoustic wave data; and
   determining the swing gesture characteristic of the player in the motion process based on the classification of the hand action of the player in the motion process and the action parameters of the hand action and based on the effective hitting and missing recognition performed on each hand action.

4. The action recognition method according to claim 1, wherein the third motion data comprises a motion image of the player, and the obtaining an image action characteristic of the player in the motion process comprises:
   inputting the motion image of the player into the trained convolutional neural network model for processing, so as to obtain the image action characteristic corresponding to the motion image of the player.

5. The action recognition method according to claim 4, wherein before the inputting the motion image of the player into a trained convolutional neural network model for processing, so as to obtain the image action characteristic corresponding to the motion image of the player, the method further comprises:
selecting a target image region from the motion image of the player, wherein the target image region is an image region that comprises only the player.

6. The action recognition method according to claim 1, wherein the motion data further comprises fourth motion data, and correspondingly, the action recognition method further comprises:
determining physiological parameters of the player in the motion process based on the fourth motion data.

7. An action recognition apparatus, comprising:
a first obtaining unit, configured to obtain motion data through a short-range communication connection, wherein the short-range communication connection is at least one of a Bluetooth connection, a near field communication (NFC) connection, a wireless-fidelity (Wi-Fi) connection, or a ZigBee connection, and wherein the motion data comprises first motion data, second motion data, and third motion data, the first motion data is collected by a first data collection apparatus located at a first preset part of a player, the second motion data is collected by a second data collection apparatus disposed at a preset location of a racket, and the third motion data is collected by a third data collection apparatus disposed at a preset shooting location;
a second obtaining unit, configured to: obtain a gait characteristic of the player in a motion process based on the first motion data, obtain a swing gesture characteristic of the player in the motion process based on the second motion data, and obtain an image action characteristic of the player in the motion process based on using a trained convolutional neural network model to process the third motion data; and
a recognition unit, configured to:
recognize a hitting action of the player in the motion process based on the gait characteristic, the swing gesture characteristic, and the image action characteristic; and
when it is recognized that the hitting action is an effective smash with leg curl:
obtain a leg curl angle, a hang duration, and a jump height; and
correct the jump height based on the hang duration and the leg curl angle.

8. A motion monitoring system, wherein the motion monitoring system comprises the first data collection apparatus, the second data collection apparatus, the third data collection apparatus, and the action recognition apparatus according to claim 7;
the first data collection apparatus, the second data collection apparatus, and the third data collection apparatus are separately communicatively connected to the action recognition apparatus;
the first data collection apparatus is configured to collect first motion data;
the second data collection apparatus is configured to collect second motion data;
the third data collection apparatus is configured to collect third motion data; and
the action recognition apparatus is configured to recognize a hitting action of a player in a motion process based on the first motion data, the second motion data, and the third motion data.

9. The motion monitoring system according to claim 8, wherein the motion monitoring system further comprises a fourth data collection apparatus; the fourth data collection apparatus is communicatively connected to the action recognition apparatus;
the fourth data collection apparatus is configured to collect fourth motion data; and
the action recognition apparatus is further configured to determine physiological parameters of the player in the motion process based on the fourth motion data.

10. A terminal device, comprising a memory, a processor, and a computer program stored in the memory and running on the processor, wherein when the processor executes the computer program, the action recognition method according to claim 1 is implemented.

11. A non-transitory computer-readable storage medium, wherein the computer-readable storage medium stores a computer program, and when the computer program is executed by a processor, the action recognition method according to claim 1 is implemented.

12. A chip, comprising a processor, wherein the processor is coupled to a memory, the memory is configured to store computer program instructions, and when the processor executes the computer program instructions, the chip is enabled to perform the action recognition method according to claim 1.

* * * * *